(12) United States Patent
Liu

(10) Patent No.: US 12,083,296 B2
(45) Date of Patent: Sep. 10, 2024

(54) KINK RESISTANT PEEL AWAY SHEATH

(71) Applicant: Abiomed, Inc., Danvers, MA (US)

(72) Inventor: Clifford M. Liu, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 929 days.

(21) Appl. No.: 16/707,923

(22) Filed: Dec. 9, 2019

(65) Prior Publication Data

US 2020/0179657 A1 Jun. 11, 2020

Related U.S. Application Data

(60) Provisional application No. 62/777,598, filed on Dec. 10, 2018.

(51) Int. Cl.
*A61M 25/06* (2006.01)
*A61L 29/08* (2006.01)
*A61M 25/00* (2006.01)
*A61M 25/01* (2006.01)

(52) U.S. Cl.
CPC ........ *A61M 25/0668* (2013.01); *A61L 29/085* (2013.01); *A61M 25/005* (2013.01); *A61M 2025/0188* (2013.01)

(58) Field of Classification Search
CPC ............ A61M 25/0668; A61M 25/005; A61M 25/0012; A61M 25/0045;
(Continued)

(56) References Cited

U.S. PATENT DOCUMENTS

2005/0182387 A1* 8/2005 Webler .............. A61M 25/0668
604/164.05
2009/0043285 A1 2/2009 Stehr et al.
(Continued)

FOREIGN PATENT DOCUMENTS

CN 105682725 A 6/2016
DE 19827832 A1 12/1999
(Continued)

OTHER PUBLICATIONS

International Search Report and Written Opinion for Application No. PCT/US2019/065139 dated May 11, 2020.
(Continued)

*Primary Examiner* — Dianne Dornbusch
(74) *Attorney, Agent, or Firm* — Botos Churchill IP Law LLP

(57) ABSTRACT

Devices and methods for providing a kink resistant peel away sheath are disclosed. One device includes a sheath for insertion into a vasculature of a patient. The sheath comprises a sheath body having an outer surface, a longitudinal axis and a lumen formed therethrough. The sheath body comprises an inner layer arranged about the longitudinal axis, an outer layer coaxially arranged with the inner layer, and a support layer positioned between the inner and outer layers, wherein the inner, outer and support layers are laminated together to form the sheath body. The sheath also comprises at least one shear line positioned beneath the outer surface of the sheath body, and configured to facilitate the longitudinal separation of the sheath body along the at least one shear line.

22 Claims, 9 Drawing Sheets

(58) Field of Classification Search
CPC ... A61M 2025/0188; A61M 2025/0024; A61L 29/005
See application file for complete search history.

(56) References Cited

U.S. PATENT DOCUMENTS

| | | | |
|---|---|---|---|
| 2010/0059173 A1* | 3/2010 | Kampa | B29D 23/001 156/244.15 |
| 2010/0268196 A1 | 10/2010 | Hastings et al. | |
| 2010/0312222 A1 | 12/2010 | Leeflang et al. | |
| 2014/0236122 A1 | 8/2014 | Anderson et al. | |
| 2014/0236123 A1 | 8/2014 | Birmingham et al. | |

FOREIGN PATENT DOCUMENTS

| | | |
|---|---|---|
| EP | 1870125 A1 | 12/2007 |
| JP | 2008264104 A | 11/2008 |
| JP | 2008543440 A | 12/2008 |
| JP | 2010227138 A | 10/2010 |
| WO | 2006138356 A2 | 12/2006 |

OTHER PUBLICATIONS

Office Action from corresponding Chinese Application No. 2019800889524 dated Jan. 19, 2023 (25 pp.).
Office Action from corresponding Indian Patent Application No. 202117029737 dated Feb. 9, 2023 (7 pages).
Office Action from corresponding Chinese Patent Application No. 2019800889524 dated Sep. 27, 2023 (25 pp.).
Office Action from corresponding Japanese Patent Application No. 2021-532845 dated Nov. 8, 2023 (10 pp.).
Office Action from corresponding Japanese Patent Application No. 2021-532845 dated Mar. 1, 2024 (4 pp.).

* cited by examiner

KINK RESISTANT PEEL AWAY SHEATH

CROSS-REFERENCE TO RELATED APPLICATION

This application claims the benefit of priority to U.S. Provisional Application No. 62/777,598, filed on Dec. 10, 2018. The specification of the foregoing application is hereby incorporated by reference in its entirety.

BACKGROUND

Intravascular medical devices may comprise, but are not limited to, an Impella® pump, an Extracorporeal Membrane Oxygenation (ECMO) pump, and a balloon pump. The Impella® pump may further comprise an Impella 2.5® pump, an Impella 5.0® pump, an Impella CP® pump and an Impella LD® pump, all of which are by Abiomed, Inc. of Danvers, MA Peel away introducers are disposable medical devices used in a cardiac catheterization or other medical setting to deliver medical devices into the vasculature of a patient. The medical device is usually threaded through the peel away sheath prior to insertion of the medical device into the patient's vasculature. Once the medical device has been positioned, the peel away introducer can removed. Such removal is needed so that other medical devices larger than the lumen in the sheath (and hub) can be inserted into the arteriotomy of the patient. Standard peel away introducers include a proximal plastic hub coupled to a sheath that enable the sheath to be peeled away. Medical devices can be inserted through the plastic huh and into the sheath, through which the device can be placed in a patient's body. Intravascular medical devices, such as intracardiac blood pumps, catheters, guidewires, or leads, can be introduced into a patient's vasculature through a peel away introducer.

In one approach, the physician peels away the sheath of the introducer by cracking the plastic introducer hub (if present) and peeling down the shaft of the sheath body. In order to peel away the sheath of the introducer, a separating force needs to be applied to the sheath body. The physician then grasps the hub and breaks it at the proximal end of the sheath along axial notches or scorings. The sheath tears along its longitudinal axis, along shear lines or scorings down one or both sides of the sheath and can be peeled axially. The peel away sheath of the introducer allows the introducer to be moved out of the way or removed, after a medical device is inserted into a patient through the introducer, without disturbing or removing the medical device.

In a common manufacturing technique, peel away sheaths are formed from a single extruded plastic tube. Such extruded plastic tubes are usually rigid and are positioned in the patient using a dilator. Once inserted into the vasculature of the patient, the dilator is removed. For complex medical procedures, it may be necessary to reposition the sheath, or place additional lateral (pushing) force on the sheath, e.g. to secure it further to the patient. This causes the extruded tube to kink or bend, thereby obstructing the passageway in the sheath, which adds to complicates the medical procedure. Further, due to the nature of currently available sheaths, additional procedures are required to prevent the sheath from forming kinks. Such procedures include suturing or taping the sheath in a desired position to prevent it from collapsing or bending. The additional steps complicate the use of the sheath and also increase the overall profile of such procedures.

SUMMARY

Disclosed herein are approaches for addressing various problems and shortcomings of the state of the art, as identified above. More particularly, disclosed herein are devices and methods for providing a kink resistant peel away sheath. In one embodiment, the device comprises a sheath for insertion into a vasculature of a patient. The sheath comprises a sheath body having an outer surface, a longitudinal axis and a lumen formed therethrough. The sheath body comprises an inner layer arranged about the longitudinal axis, an outer layer coaxially arranged with the inner layer, and a support layer positioned between the inner and outer layers, wherein the inner, outer and support layers are laminated together to form the sheath body. The sheath also comprises at least one shear line formed in the sheath body, the at least one shear line positioned beneath the outer surface of the sheath body, and configured to facilitate the longitudinal separation of the sheath body along the at least one shear line.

The support structure enables the sheath to withstand large pushing forces without forming kinks. This gives rise to a sheath with greater pushability while maintaining flexibility for complex intravascular procedures. Further, the formation of shear lines in the sheath structure ensures that the kink resistant sheath can be separated easily.

In some implementations, the support layer is coaxially arranged between the inner and outer layers. Such coaxial arrangement ensures layers of similar thickness about the circumference of the sheath body. In certain implementations, the inner and outer layers comprise extrusions. In some implementations, the inner and outer layers are fabricated from any one of: a polyether block amide (such as PEBAX or PebaSlix®), a polyethylene material, a polytetrafluoroethylene (PTFE) material, a high-density polyethylene (HDPE) material, medium-density polyethylene (MDPE) material, and a low-density polyethylene (LDPE) material.

In some implementations, the shear line may be linear or non-linear. In certain implementations, each shear line may be formed by a monofilament positioned between any one of: the inner and support layers, and the support and outer layers, before the inner, outer and support layers are laminated. In further implementations the monofilament may be fabricated from a material with a melting point that is higher, the same as, or lower than the melting point of the materials used for the inner and outer layers. In some implementations, the monofilament extends longitudinally along the sheath body. In certain implementations, the monofilament helically extends along the longitudinal axis. Such variations allows for the fabrication of kink resistant sheaths that suit the physician's needs based on the medical procedure at hand.

In certain implementations, the monofilament may comprises a rod fabricated from any one of: polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (MDPE) material, a low-density polyethylene (LDPE) material, and stainless steel.

In some implementations, the monofilament may fuse with the support layer. In further implementations, the sheath comprises two shear lines, thereby making peel away of the kink resistant sheath easy. In certain implementations, the monofilaments may be radially separated 180° about the longitudinal axis of the sheath. In further implementations, a void may develop between the monofilament and at least one of the inner layer and the outer layer. In some implementations, the monofilament may be removable from the sheath body. The removal of the monofilaments leaves a void in the sheath body which allows the kink resistant sheath to be easily split.

In certain implementations, the at least one shear line may comprise at least one weak joint formed by: splitting the sheath body along the longitudinal axis, and reflowing the split sheath body to create the at least one weak joint that reconnects the split sheath body. In some implementations, the at least one shear line may comprise a plurality of weak joints formed by: splitting the sheath body along the longitudinal axis into a plurality of portions, inserting a thin extrusion layer into the lumen of the sheath body, and reflowing the split sheath body with the thin extrusion layer to create the plurality of weak joints that reconnects the split sheath body. Such alternatives to the formation of the shear line provide for kink resistant sheaths that are easier to fabricate yet still allow for larger pushing forces to be applied without causing the sheath to kink or collapse. In further implementations, the support layer may comprises a braid or a coil. In some implementations, the support layer may comprise a spiral laser cut layer. In certain implementations, the sheath body may be pre-scored along the shear line. This eases separation of the sheath body as the physician would require less force to peel away the sheath.

In some implementations, the support layer may comprise at least one S-shaped wire having turns that are held in an interlocked orientation by a removable mandrel. In other implementations, the support layer may comprise a plurality of S-shaped wires that are held in an interlocked orientation by a corresponding number of removable mandrels. Such S-wires offer an alternative support structure whereby the interlocking wires serve to both hold the S-wires in place during lamination, and provide for a shear line after lamination once they are removed from the sheath body.

In certain implementations, the at least one shear line may be positioned within at least one of the following: the inner layer, the outer layer and the support layer. In other implementations, the at least one shear line may extend longitudinally along at leak a portion of the length of the sheath body. In some implementations, the at least one shear line may comprise any one of: a void, a frangible seam, and a frangible connection, formed within the sheath body. In certain implementations, the support layer may be fabricated from any one of: polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (HDPE) material, a low-density polyethylene (LDPE) material, and stainless steel.

In another embodiment, a method for fabricating a kink resistant peel away sheath is described. The method comprises the step of providing a tubular inner layer having a longitudinal axis and a lumen formed therethrough. The method then includes the step of providing an outer layer coaxially arranged with the inner layer. The next step in the method is the provision of a support layer laminated between the inner and outer layers to form a sheath body. The method also includes the step of reflowing the sheath body to fuse the inner, outer and support layers. The next step in the method is the forming at least one shear line positioned beneath the outer surface of the sheath body, and the at least one shear line configured to facilitate the longitudinal separation of the sheath body along the at least one shear line.

In some implementations, the method further comprises the step of arranging the support layer coaxially between the inner and outer layers. In other implementations, the method comprises the step of inserting at least one monofilament between the inner and support layers, or between the support and outer layers, before reflowing the sheath body. In certain implementations, the method also comprises the step of removing the monofilament after reflow. In some implementations, the monofilament may comprise a rod fabricated from any one of: polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (MDPE) material, a low-density polyethylene (LDPE) material, and stainless steel. In certain implementations, the sheath comprises two shear lines.

In some implementations, the method may further comprise the step of scoring the sheath body before reflowing. In other implementations, the method may further comprise the step of radially separating the monofilaments by 180° about the longitudinal axis. In certain implementations, the method additionally comprises the steps of splitting the sheath body along the longitudinal axis, and reflowing the split sheath body to create at least one weak joint that reconnects the split sheath body. In some implementations, the step of forming each shear line in the sheath body further comprises the steps of splitting the sheath body along the longitudinal axis, inserting a thin extrusion layer into the lumen of the sheath body, and reflowing the split sheath body to create at least one weak joint that reconnects the split sheath body.

In other implementations, the step of providing a support layer laminated between the inner and outer layers further comprises the step of interlocking a plurality of S-shaped wires wrapped around the inner layer by a corresponding number of removable mandrels, wherein each mandrel is removable to form the shear line in the sheath body.

In a further embodiment, there is provided a sheath body having an outer surface, a longitudinal axis and a lumen formed therethrough. Also provided is a support means laminated within the sheath body and extending longitudinally along the sheath body, and a shear means positioned beneath the outer surface of the sheath body, the shear means configured to facilitate the longitudinal separation of the sheath body along the at least one shear means.

In some implementations, the support means may comprise a support layer. In other implementations, the shear means may comprise at least one shear line. In further implementations, the sheath body may comprise an inner layer arranged about the longitudinal axis, an outer layer coaxially arranged with the inner layer, and wherein the support means is laminated between the inner and outer layers. In some implementations, the support means may be coaxially arranged between the inner and outer layers. In other implementations, the inner and outer layers may comprise extrusions.

In certain implementations, the inner and outer layers may be fabricated from any one of: a polyether block amide (such as PEBAX or PebaSlix®), a polyethylene material, a polytetrafluoroethylene (PTFE) material, a high-density polyethylene (HDPE) material, a medium-density polyethylene (MDPE) material, and a low-density polyethylene (LDPE) material.

In some implementations, the at least one shear line may be linear or non-linear. In certain implementations, each shear line may be formed by a monofilament positioned between any one of: the inner and support layers, and the support and outer layers, before the inner, outer and support layers are laminated. In other implementations, the monofilament may be fabricated from a material with a melting point that is higher, the same as, or lower than the melting point of the materials used for the inner and outer layers. In some implementations, the monofilament may extend longitudinally along the sheath body. In certain implementations, the monofilament may helically extend along the longitudinal axis.

In further implementations, the monofilament may comprise a rod fabricated from any one of: polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (MDPE) material, a low-density polyethylene (LDPE) material, and stainless steel. In some implementations, the monofilament may fuse with the support layer. In other implementations, the sheath may comprise two shear lines. In other implementations, the monofilaments may be radially separated 180° about the longitudinal axis. In certain implementations, a void may develop between the monofilament and at least one of the inner layer and the outer layer. In some implementations, the monofilament may be removable from the sheath body.

In some implementations, the at least one shear line may comprise at least one weak joint formed by: splitting the sheath body along the longitudinal axis, and reflowing the split sheath body to create the at least one weak joint that reconnects the split sheath body. In other implementations, the at least one shear line may comprise a plurality of weak joints formed by: splitting the sheath body along the longitudinal axis into a plurality of portions, inserting a thin extrusion layer into the lumen of the sheath body, and reflowing the split sheath body with the thin extrusion layer to create the plurality of weak joints that reconnects the split sheath body.

In certain implementations, the support layer may comprise a braid or a coil. In other implementations, the support layer may comprise a spiral laser cut layer. In further implementations, the sheath body may be pre-scored along the shear line. In some implementations, the support layer may comprise at least one S-shaped wire having turns that are held in an interlocked orientation by a removable mandrel. In other implementations, the support layer may comprise a plurality of S-shaped wires that are held in an interlocked orientation by a corresponding number of removable mandrels.

In some implementations, the at least one shear line may be positioned within at least one of the following: the inner layer, the outer layer and the support layer. In certain implementations, the at least one shear line may extend longitudinally along at leak a portion of the length of the sheath body. In further implementations, the at least one shear line may comprise any one of: a void, a frangible seam, and a frangible connection, formed within the sheath body.

In other implementations, the support layer may be fabricated from any one of: polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (HDPE) material, a low-density polyethylene (LDPE) material, and stainless steel.

In another embodiment, there is provided a method of using the aforementioned sheaths for treating a patient with a ventricular assist device. The method comprises the step of inserting the sheath into the arteriotomy of the patient at a first position. Next the method comprises the step of separating the sheath by peeling away the sheath body. Finally, the method comprises the step of inserting the ventricular assist device into the arteriotomy of the patient at the first position.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
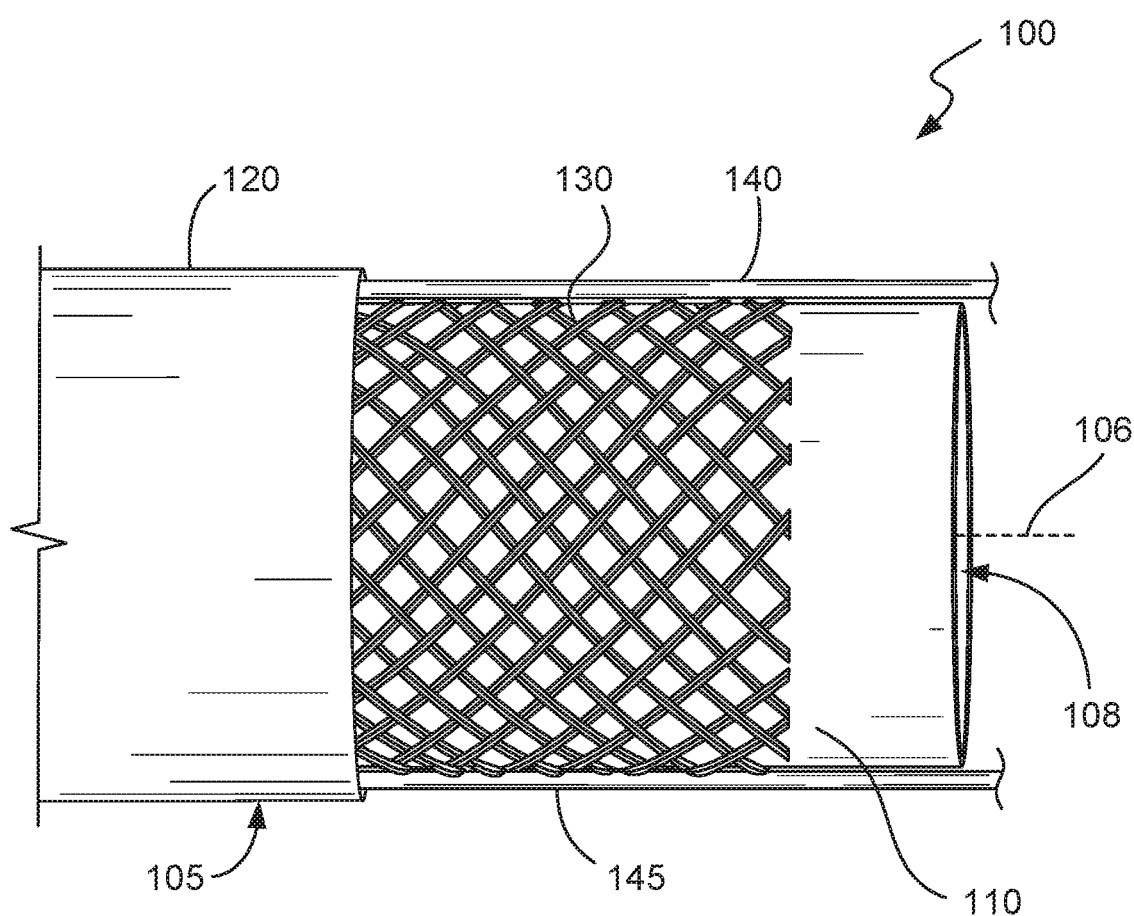
FIG. 1 shows an illustrative peel away sheath according to an embodiment of the present discloser.

To provide an overall understanding of the devices and methods described herein, certain illustrative embodiments will be described. Although the embodiments and features described herein are specifically described for use in connection with kink resistant peel away sheaths for use in intravascular procedures involving ventricular assist devices, it will be understood that all the components and other features outlined below may be combined with one another in any suitable manner and may be adapted and applied to other types of procedures requiring a kink resistant peel away sheath.

The devices and methods described herein use a sheath structure that comprises inner and outer layers, and a support layer to reinforce the sheath. These layers are subject to a heat treatment (reflow) such that lamination of the layers occurs where the layers laminate together. Such a reinforced laminated structure allows for the sheath to be subject to larger pushing forces without causing the sheath to kink or collapse.

The sheath may also include monofilaments or rods, such as nylon rods, that are inserted into the layered structure of the sheath body, positioned between the outer and support layers. During the lamination process, the monofilaments do not fuse with the inner and outer layers of the sheath body thereby allowing them to be removed after the heat treatment. When the monofilaments are removed, voids remain in their place. Such voids cause the sheath body to thin in the immediate vicinity of the voids, thereby forming shear lines within the sheath body about which the sheath would separate or peel away when subjected to a separating force, e.g. when a physician pulls apart the sheath. The sheath body would peel away along the shear lines in a controlled and predetermined manner.

In other embodiments, the shear lines may be formed by frangible seams. Here the laminated sheath body may be split along its longitudinal axis into at least two portions. The split portions of the sheath body may then be reassembled and reflowed once again to cause a frangible seam to form between the two split portions of the sheath body (due to melting of the split portions, for example). The frangible seams are formed within the sheath body and beneath the outer surface of the sheath body. Such frangible seams require smaller separation forces to break, thereby allowing the reinforced sheath to be peeled away easily. In further embodiments, the split portions of the seam may be reassembled onto a single extruded layer. The reassembled structure may then be subject to an additional reflow process such that the split portions of the sheath body are fused to the outer surface of the single extruded layer, thereby forming frangible connections. As with the seams, the frangible connections are thinner than the thickness of the layered sheath body, and so smaller separation forces are required to break the connections, thereby allowing the reinforced sheath to be peeled away easily. The frangible connections are also formed beneath the outer surface of the sheath body.

The reinforced laminated structure of the sheath body and the shear lines formed thereon result in a flexible peel away sheath that is able to withstand larger forces, such as, but not limited to, pushing forces. The increased pushability of such sheaths enable their use without the need for a hub as described in the foregoing, thereby reducing the profile of the kink resistant peel away sheath.

FIG. 1 shows an expanded view of an illustrative kink resistant sheath 100 according to an embodiment of the present disclosure. The sheath 100 is suitable for insertion into the arteriotomy of a patient, such as the femoral artery. The sheath 100 comprises a sheath body 105 extending along a longitudinal axis 106 and having a lumen 108 extending therethrough. In certain embodiments, the sheath body 105 may be tubular with a circular cross section, however the sheath body 105 may be of any shape and configuration.

The lumen of the sheath body 105 is open for the passage of a ventricular assist device such as a percutaneous pump (not shown). An example of such a percutaneous pump is the Impella 2.5™ pump system from Abiomed, Inc. of Danvers, Massachusetts Such a pump generally comprises a catheter body with a pump head at a distal end of the catheter body and a handle at a proximal end of the catheter body. In most situations the pump head would have a larger diameter than the diameter of the catheter body. It will be understood that while a percutaneous heart pump is described herein, any other percutaneous or intravascular medical device can be used in conjunction with the present disclosure.

The sheath body 105 comprises an inner layer 110 arranged along the longitudinal axis 106 of the sheath body 105. Inner layer 110 may comprise an extruded layer having a lumen formed therethrough. The lumen of the inner layer 110 forms the lumen of the sheath body 105. The inner layer 110 may comprise a first material. In some embodiments the inner layer 110 may be tubular with a circular cross section, an inner surface, and outer surface. The sheath body 105 may also comprise an outer layer 120. As with the inner layer 110, the outer layer 120 may comprise an extruded layer. The outer layer 120 may comprise a second material. In some embodiments the outer layer 120 may be tubular with a circular cross section, an inner surface, and outer surface. The outer layer 120 is arranged about the longitudinal axis 106 of the sheath body 105 such that the outer layer 120 is coaxial with respect to the inner layer 110. In this configuration the outer layer 120 is concentrically arranged around the inner layer 110 along the length of the sheath body 105. In some embodiments, the outer layer 120 may be concentrically arranged around the inner layer 110 along a portion of the length of the sheath body 105.

The sheath 100 further comprises a support layer 130 arranged between the inner layer 110 and the outer layer 120. In this configuration the support layer 130 is effectively sandwiched between the first layer 110 and the second layer 120. The support layer 130 may comprise a braid structure that reinforces the inner layer 110 and outer layer 120 of the sheath body 105. The support structure 130 may be tubular with a circular cross section. In some embodiments, the support layer 130 may extend along the length of the sheath body 105. In other embodiments, the support layer 130 may extend along a portion of the length of the sheath body 105. While FIG. 1 illustrates the support layer 130 as a tubular braid structure, it will be understood that the support layer 130 may comprise other structures, such as, for example, the support layer of FIGS. 5A-5B in the following description. For example, the support structure 130 may comprise a tubular coil, or at least one S-wire wound around the outer surface of the inner layer 110 that is releasably interlocked with a corresponding number of mandrels. Such reinforcement prevents the sheath 110 from developing kinks as it is inserted or pushed into the patient's vasculature, while maintaining its flexibility. Further, the support layer 130 may comprise a laser cut extrusion. The laser cut extrusion may include a spiral laser cut extrusion. The laser cut extrusion may be cut according to any pattern that enhances the pushability of the sheath while keeping it flexible. By pushability, what is meant is that the structure of the peel away sheath according to the present disclosure allows for a larger pushing force to be applied to the sheath when inserting the sheathing into the vasculature of the patient without the sheath forming kinks or bends. The support structure may comprise a third material.

In some embodiments, the thickness of the inner layer 110 may be equal to the thickness of the outer layer 120. In other embodiments, the inner layer 110 and the outer layer 120 may be of different thicknesses so as to control the rigidity of the sheath 100. Further, in some embodiments the support layer 130 may be thinner than that of the inner layer 110 and the outer layer 120. In certain embodiments, inner layer 110 and outer layer 120 may comprise extrusions.

In some embodiments the first material used for the inner layer 110 may comprise any one of a polyether block amide (such as PEBAX or PebaSlix®), a polyethylene material, polytetrafluoroethylene (PTFE) material, a high-density polyethylene (HDPE) material medium-density polyethylene (MDPE) material, and a low-density polyethylene (LDPE) material. In some embodiments, the second material used for the outer layer 120 may comprise the first material, i.e. the inner layer 110 and the outer layer 120 may be made from the same material. Further, in certain embodiments, the third material used for the support layer 130 may comprise any one of polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (MDPE) material, a low-density polyethylene (LDPE) material, and stainless steel.

FIG. 1 also shows two monofilaments or rods 140, 145 that are arranged with the support layer 130 between the inner layer 110 and the outer layer 120. In some embodiments the rods 140, 145 are arranged between the outer layer 120 and the support layer 130. In other embodiments the rods 140, 145 may be arranged between the inner layer 110 and the support layer 130. Rods 140, 145 may be radially symmetric about the longitudinal axis 106 of the sheath body 105. As shown in FIG. 1, the rods 140, 145 are radially separated from each other by 180° about the longitudinal axis 106 of the sheath 100. In certain embodiments, rods 140, 145 may be fabricated from the same material type as the support layer 130, i.e. the rods 140, 145 may be fabricated from the third material as defined in the foregoing. In some embodiments, rods 140, 145 may comprise nylon rods that extend longitudinally about the axis 106. It will be understood that while two rods are shown in FIG. 1, any number of rods may be included in the sheath 100 according to the present disclosure. Additionally, in the following description, nylon rods are exemplified in the various embodiments. However it will be understood that rods of any material type as defined by the third material type may be used.

It should be noted that due to the different materials used for the rods compared to that used for the inner, outer and support layers, after lamination, a space develops in the immediate vicinity of the rods in the sheath 100. In some embodiments such a space facilitates the removal of the rods during use of the sheath.

In certain embodiments the layered arrangement illustrated in FIG. 1 is subjected to a reflow cycle where the layered configuration is exposed to heat according to a temperature profile. The heat may be implemented as a heat zone that moves along the length of the sheath body 105. The heat treatment causes the inner layer 110, outer layer 120 and support layer 130 to laminate together to form the sheath body 105 as a single layer. The laminating of the layers increases the flexibility and pushability of the sheath 100 while preventing kinks from forming in the sheath body 105. Although the reflow causes the inner layer 110, outer layer 120 and support layer 130 to be laminated together, the different material types used for these layers prevents the support layer 130 from fusing with the inner layer 110 and outer layer 120 after reflow. This results in the development of points of weakness along the length of the sheath body 105, between the inner layer 110 and the support layer 130, and between the support layer 130 and the outer layer 120.

The reflow cycle may have several variables such as peak reflow temperature, length of the heat zone, speed of the heat zone and indwell time, for example. Exemplary peak reflow temperatures include about 150° C. to about 350° C. for nylon, about 220° C. to about 290° C. for PEBAX, and about 110° C. to about 126° C. for polyethylene. In certain embodiments, the peak reflow temperature used in the reflow cycle is dependent on the length of the heat zone and/or the speed of the heat zone with reference to the sheath body 105. It should be noted that the term "about" indicates a range of ±20% of the stated value. In certain embodiments, the maximum temperature of the reflow cycle may be lower than the melting point of the material used for the rods. As such the rods 140, 145 do not fuse with the inner layer 110, outer layer 120 and the support layer 130 during reflow. In some embodiments, the rods 140, 145 may be removed from the sheath body 105 after reflow, leaving a void 142, 146 (shown in FIG. 2). In other embodiments, the maximum temperature of the reflow cycle may be higher than the melting point of the material used for the rods 140, 145. In some embodiments, the maximum temperature of the reflow cycle may be the same as the melting point of the material used for the rods 140, 145.

In some embodiments, rods 140, 145 may be fabricated from the same material type as the support layer 130. In such embodiments, the rods 140, 145 and the support layer 130 fuse together during reflow. This forms a composite support structure within the sheath body 105. This composite support structure would also have points of weakness along the length of the sheath body 105, between the inner layer 110 and the composite support structure, and between the composite support structure and the outer layer 120.

In relation to the various embodiments of the present disclosure, the presence of the rods 140, 145 in the reflowed sheath body 105 results in the formation of voids 142, 146 along the length of the sheath body 105. As previously described, the voids 142, 146 extend longitudinally along the length of the rods 140, 145 as they are located within the sheath body 105. The voids 142, 146 may thus develop between the inner layer 110 and the support layer 130, and between the support layer 130 and the outer layer 120. Further, as previously described, such surrounding material can be any one of the first, second or third material types, depending on the position of the rods 140, 145 prior to reflow. Thus, during reflow, voids 142, 146 may develop between the rods 140, 145 and the surrounding material of the sheath body 105. While it has been described that the rods 140, 145 may be removed from the sheath body 105 after reflow, this may not always been the case. In certain embodiments, the rods 140, 145 may remain in the sheath body 105 during use. It will be understood that although the rods 140, 145 remain the in the sheath body 105, voids 142, 146 still exist after reflow, however these voids 142, 146 are filled with the rods 140, 145 if they are not removed from the sheath body 105 after reflow. The voids 142, 146 therefore serve as shear lines 144, 148 that extend longitudinally in the sheath body 105 about which the sheath body 105 separates when subjected to a separating force. Such shear lines 144, 148 extend longitudinally along the sheath body 105 and are positioned below the outer surface of the sheath body 105. The voids 142, 146 therefore aid in the separation of the sheath body 105 when the sheath is subjected to a separating force.

Figure 2:
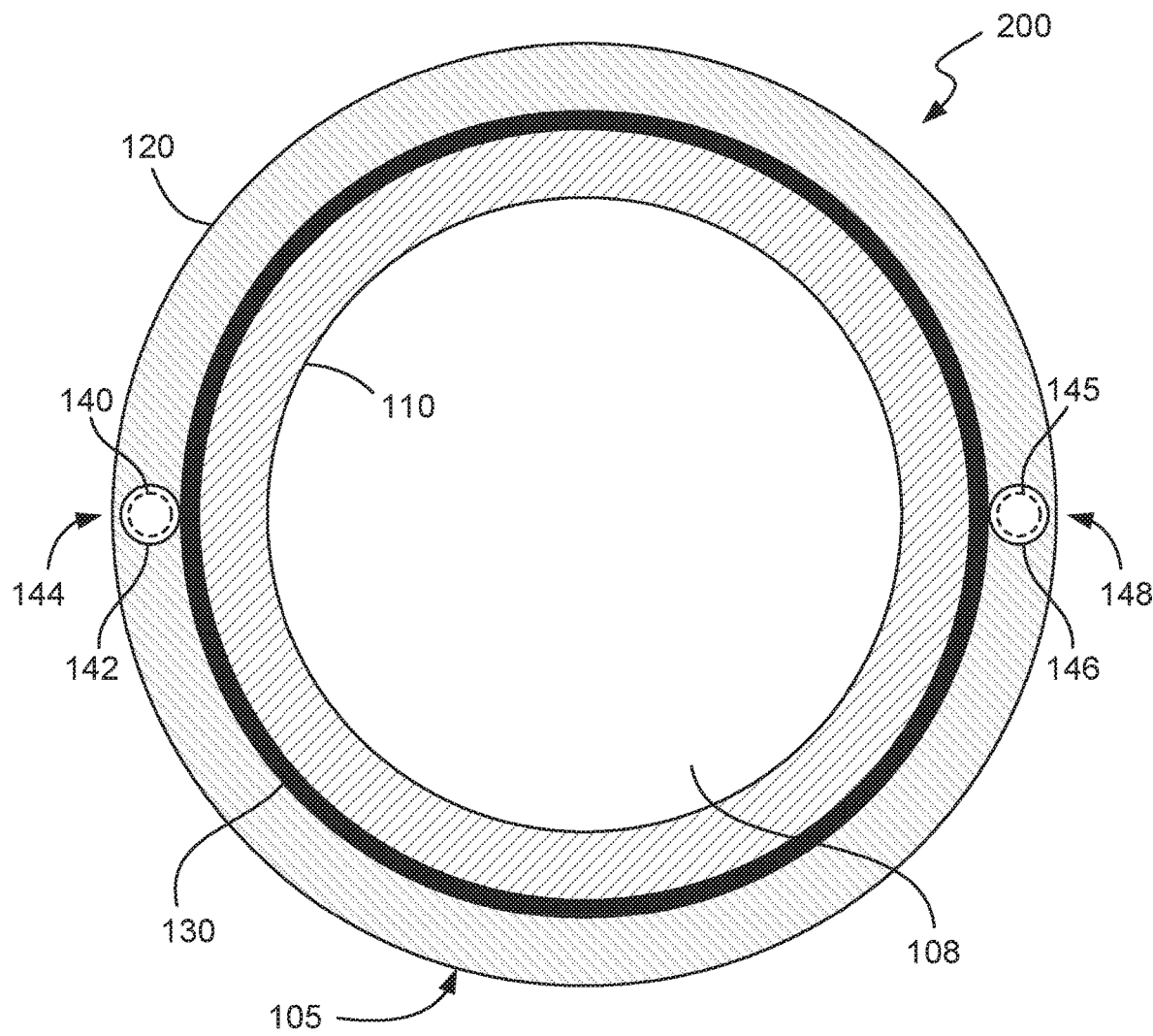
FIG. 2 shows an illustrative cross section of the peel away sheath of FIG. 1.

FIG. 2 shows the cross section 200 of the kink resistant sheath 100 in FIG. 1 after the layers 110, 120, 130 have been reflowed, and after the nylon rods 140, 145 have been removed, leaving voids 142, 146 that extend longitudinally along the length of the sheath body 105. As can be seen from the cross section in FIG. 2, once the nylon rods 140, 145 are removed from the sheath body 105, the amount of material that remains in proximity of the voids 142, 146 is reduced compared to other sections of the sheath body 105. This thinning of material of the sheath body 105 reduces the mechanical strength of the sheath body 105 in the proximity of the voids 142, 146. Thus when the sheath body 105 is subjected to separating forces, e.g. when a physician attempts to pull apart the sheath 100, the reduced mechanical strength of the sheath body 105 along the voids 142, 146 cause the sheath to fear 100 apart longitudinally along the voids 142, 146. In effect the voids 142, 146 reduce the mechanical strength of the sheath body 105 at a desired location on purpose so that the tearing of the sheath body 105 is controlled and localized such that it occurs only along the voids 142, 146. The voids 142, 146 therefore serve as shear lines 144, 148 that extend longitudinally in the sheath body 105 about which the sheath body 105 separates when subjected to a separating force. In some embodiments, the voids 142, 146 may extend longitudinally only along a portion of the length of the sheath body 105.

Further, in certain embodiments, the voids 142, 146 may be positioned in or between at least one of the inner layer 110, the outer layer 120, and the support layer 130, based on the above described reflow cycle and material types. For example, the voids 142, 146 may be formed in the inner layer 110 only, in the outer layer 120 only, in the support layer 130 only, between the inner layer 110 and the support layer 130, between the outer layer 120 and the support layer 130, or in all three layers. In any case, as the voids 142, 146 are formed within the sheath body 105, the shear lines 144, 148 are not formed on the outer surface of the sheath body 105. Instead the shear lines 144, 148 are formed beneath the outer surface and within the sheath body 105.

Additionally, the outer surface of the sheath body 105 may be pre-scored adjacent the voids 142, 146. Such pre-scoring may be done with a razor blade. Although not shown in FIG. 2, a pre-scored line would form a longitudinal grove in the outer surface of the sheath body 105 that aligns with shear lines 144, 148. Any separating forces applied to the sheath body 105 will therefore cause the sheath body to shear along the shear lines 144, 148, thereby causing longitudinal separation of the sheath body 105 along the shear lines 144, 148. While FIGS. 1 and 2 depict sheaths with two shear lines 144, 148, it will be understood that any number of shear lines can be implemented in the sheath according to the present disclosure. Thus, when the sheath 100 is pulled apart, the sheath body 105 would longitudinally separate along the shear lines 144, 148, and not elsewhere along the sheath 100. In some embodiments, the outer surface of the support layer 130 may be pre-scored, i.e. the surface of the support layer 130 in contact with the outer layer 120 may be pre-scored. Such pre-scoring may be done with a razor blade. The outer surface of the support layer 130 is pre-scored before subjecting the sheath body 105 to the reflow cycle. Pre-scoring the outer surface of the support layer 130 aids in separating the sheath body 105 when the sheath 100 is pulled apart.

Figure 3:
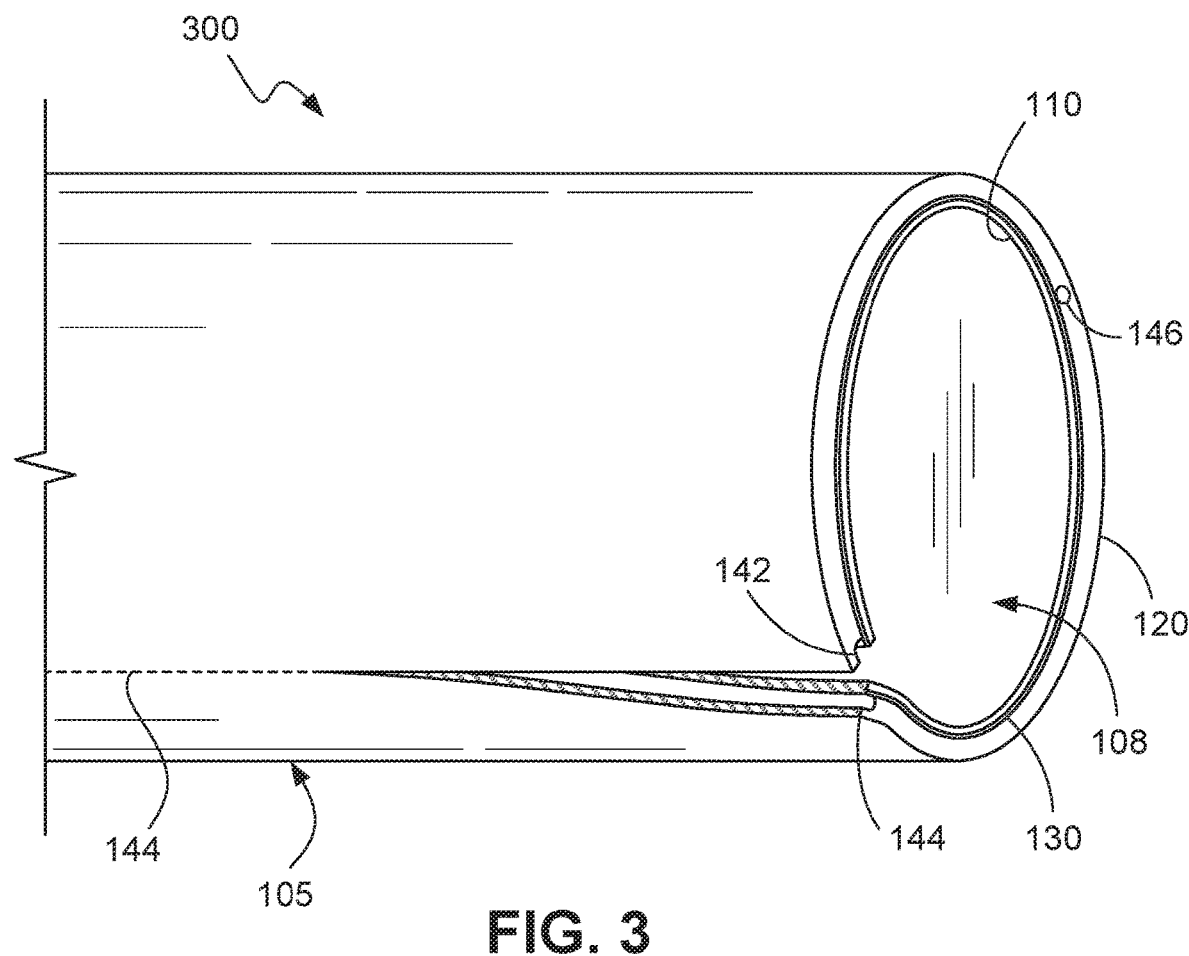
FIG. 3 shows the illustrative peel away sheath of FIGS. 1 and 2 being separated along a shear line in the sheath body.

FIG. 3 shows a sheath 300 according to an embodiment of the present disclosure when subject to a shear force that separates the sheath body. Sheath 300 comprises the same features as sheath 100 in FIG. 1. As previously mentioned such a shear force may be imparted to the sheath 300 When the sheath 300 is pulled apart. Sheath 300 comprises the same features as sheath 100 in FIG. 1, however only one shear line 144 is illustrated in the FIG. 3. Such a shear line may have been formed by removable nylon rods 140, 145 similar to those in FIGS. 1 and 2 where voids 142, 146 are formed after removal of the nylon rods 140, 145 from the sheath body 105. While shear line 144 is shown in FIG. 3 as being positioned on the outer surface of the sheath body 105, per the foregoing description, it s understood that the shear line 144 is located within the sheath body 105 and beneath the outer surface of the sheath body 105. As shown in FIG. 3, the sheath body 105 separates along the shear line 144. Such a shear line 144 is essentially formed in the sheath body 105 by the void 142. Due to the reduced amount of material in the sheath body 105 along the void 142, the force required to separate or peel away the sheath 300 is also reduced. Further, as the sheath body 105 has a support structure 130 fused within it, the sheath 300 is able to withstand pushing forces during use (e.g. when the sheath 300 is being pushed into the vasculature of a patient) without buckling or kinking.

It will be understood that the kink resistant peel away sheaths 100, 200 and 300 of FIGS. 1-3 as described in the foregoing may be implemented as introducer sheaths for the insertion of a ventricular assist device into the vasculature of a patient. When used as an introducer sheath, a distal end of the sheath body 105 may be coupled to an introducer hub, such as, for example, the introducer sheath hub described in U.S. Provisional Patent Application No. 62/672,212, and the introducer hub described in U.S. patent application Ser. No. 15/438,171, the contents of which are hereby incorporated by reference in entirety. Such introducer hubs are configured with notches and wings that enable the hub to easily split into at least two sections upon application of minimal force. When such hubs are coupled to the kink resistant peel away sheath of the present disclosure, separation of the sheath body 105 along shear lines 144, 148 would result when the hub is split, thereby enabling the controlled separation of the sheath body 105 by a physician.

Figure 4:
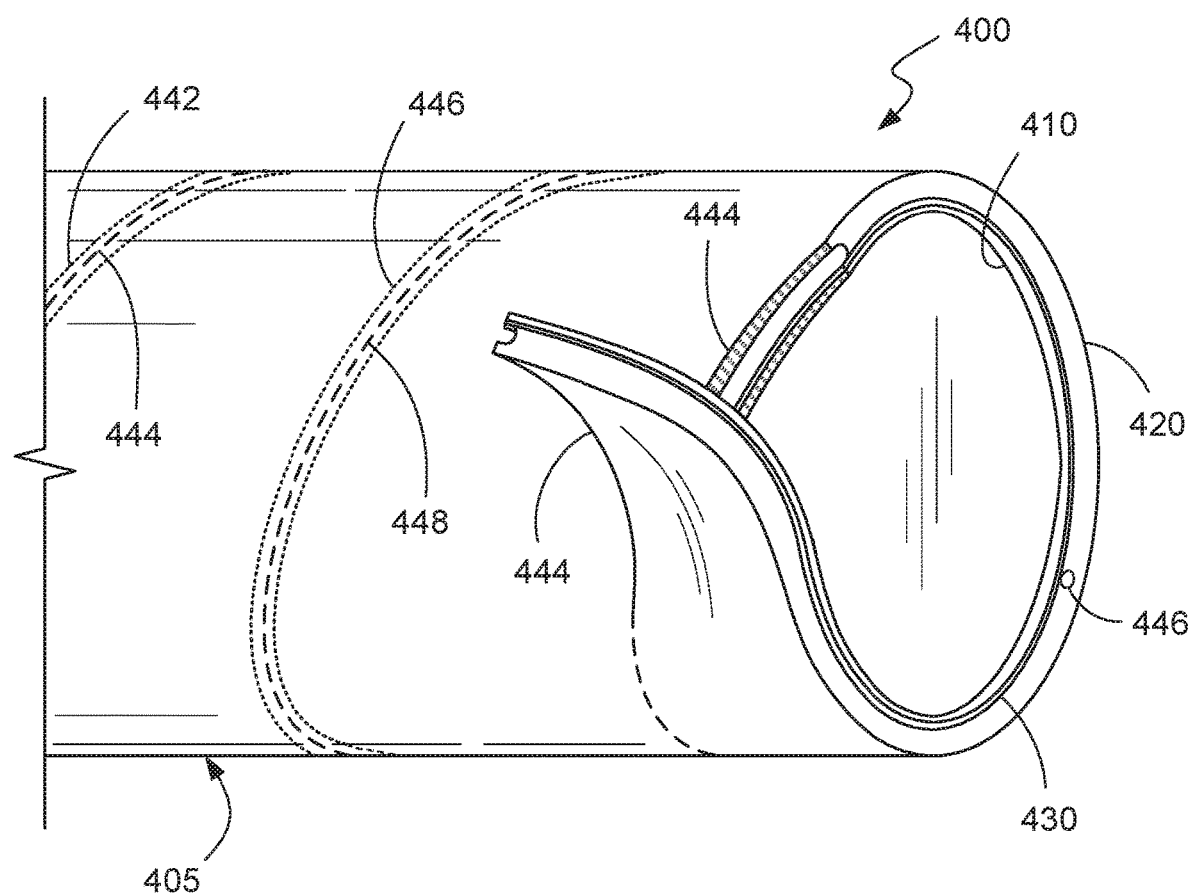
FIG. 4 shows an illustrative peel away sheath being separated along a helical shear line in the sheath body according to an embodiment of the present disclosure.

FIG. 4 shows a sheath 400 according to a further embodiment of the present disclosure. The sheath 400 comprises a sheath body 405 which has a similar structure to that of sheath body 105, i.e. sheath body 405 comprises an inner layer 410, an outer layer 420 coaxially arranged about the inner layer 410, a support layer 430 positioned between the inner layer 410 and the outer layer 420, and nylon rods. As with sheath 100, nylon rods may be positioned between the outer layer 420 and the support layer 430 in sheath 400, or between the inner layer 410 and the support layer 430. However unlike sheath 100 in FIG. 1 in which rods 140, 145 extend linearly along the longitudinal axis of the sheath body 105, in sheath 400 the rods extend helically about the longitudinal axis of the sheath body 405. In this configuration, the nylon rods effectively form a double helix that extends longitudinally about the sheath body 405. In doing so, the helically wound nylon rods add strength and rigidity to the sheath 400 which is beneficial when inserting the sheath 400 into the vasculature of the patient. This ensures that the sheath 400 does not kink when inserted into the patient. After the layered sheath body 405 and nylon rods are reflowed, voids 442, 446 form along the length of the sheath body 105. In some embodiments, the nylon rods may be removed from the sheath body 405 to leave voids 442, 446 that also extend longitudinally in a double helix manner along the sheath body 405 in place of the nylon rods. As mentioned with respect to FIG. 1, each of the voids 442, 446 form a helical shear line 444, 448 that extends longitudinally along the sheath body 405. As with sheath 100 in FIGS. 1 and 2, and sheath 300 in FIG. 3, shear line 444 is located within the sheath body 405 and beneath the outer surface of the sheath body 405. It will be understood that the helical rods disclosed in respect of the sheath 400 in FIG. 4 are not the same as a support layer comprising a coil or a laser cut spiral, as disclosed in the foregoing with respect to the sheath 100 of FIG. 1.

In order to separate the sheath body 405, instead of applying a separating force on either side of the sheath body (as in the case of sheath 100), the physician simply needs to unwrap the distal end of the sheath body 405 in order to peel away the sheath 405. Due to the shear lines that form interlaced helixes within the structure, the sheath body 405 peels away like a ribbon when subject to a shear force, as depicted in FIG. 4.

Figure 5A:
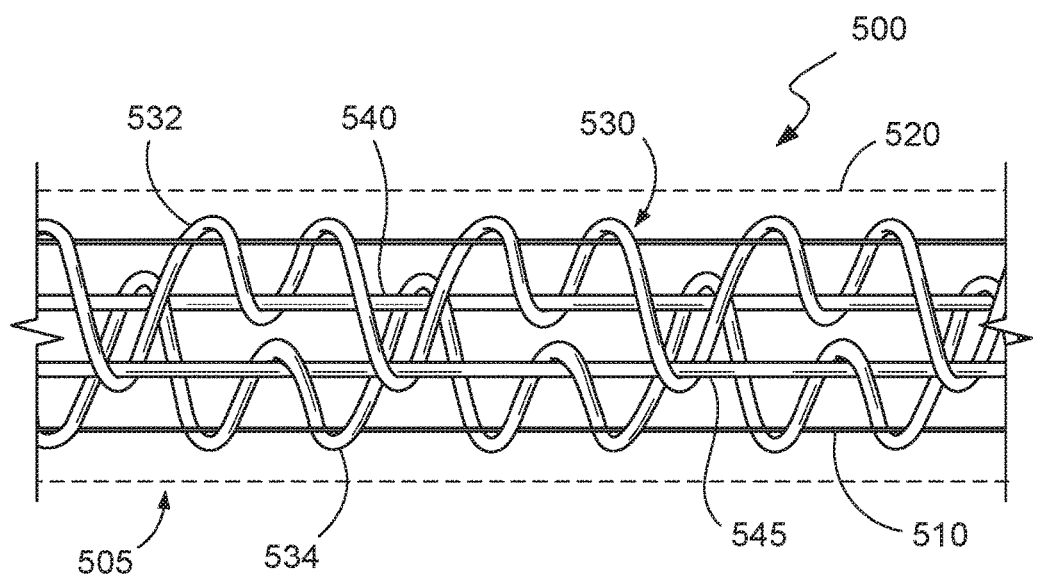
FIG. 5A shows an illustrative support layer of the peel away sheath of FIG. 1 having two S-shaped wires that are held in an interlocked orientation by two removable mandrels according to an embodiment of the present disclosure.
Figure 5B:
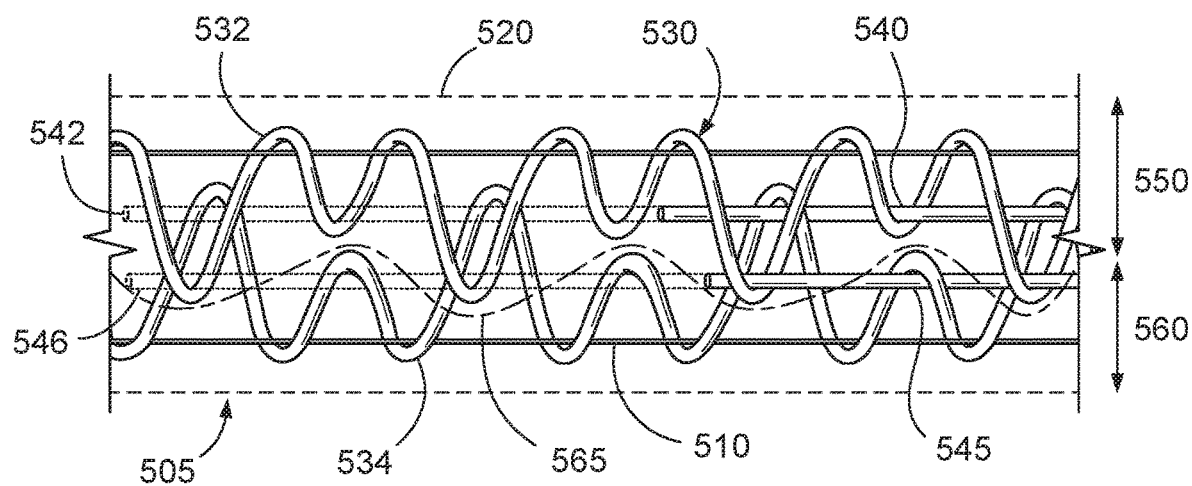
FIG. 5B shows removal of the mandrels of the support layer illustrated in FIG. 5B to separate the sheath body.

FIGS. 5A-5B shows a sheath 500 according to a further embodiment of the present disclosure. Sheath 500 comprises a sheath body 505 which comprises an inner layer 510, an outer layer 520 coaxially arranged about the inner layer 510, and a support layer 530 positioned between the inner layer 510 and the outer layer 520. FIG. 5A shows the detailed configuration of the support layer 530 according to an embodiment of the present disclosure. Unlike sheath 100 shown in FIG. 1 in which the support layer 130 comprises a tubular braid structure, the support layer 530 comprises interweaved S-wires 532, 534. The S-wires 532, 534 are additionally interlocked with mandrels 540, 545. In this configuration, S-wire 532 alternately winds over-and-under the mandrels 540, 545 in a zigzag fashion across the top half of the outer surface of the inner layer 510. Similarly, S-wire 534 alternately winds over-and-under the mandrels 540, 545 in a zigzag fashion across the bottom half of the outer surface of the inner layer 510. Further, the arrangement of the S-wires 532, 534 and mandrels 540, 545 is such that the S-wires 532, 534 are interweaved with each other about each mandrel 540, 545. Thus moving longitudinally along each mandrel 540, 545, the S-wires 532, 534 are arranged over-and-under the mandrel in an alternate fashion, as shown in FIG. 5A. In this manner, the mandrels 540, 545 lock the S-wires 532, 534 in place around the inner layer 510. While only two S-wires and two mandrels are shown in FIG. 5A, embodiments with any number of S-wires and mandrels are also included within the scope of the present disclosure.

As with the sheaths that have been described in the foregoing, the inner layer 510, outer layer 520 and support layer 530 of sheath 500 are reflowed to enable the layers to fuse together. The interwoven S-wires 532, 534 in the fused layers of the sheath body 505 increases the flexibility and pushability of the sheath 500 while preventing kinks from forming when the sheath is inserted in the vasculature of the patient. After the reflow process, the mandrels 540, 545 are extracted in a manner similar to the nylon rods as described in the foregoing. Such extraction of the mandrels 540, 545 is depicted in FIG. 5B, and leaves voids 542, 546 in the sheath body 505. The voids 542, 546 extend longitudinally along the sheath body 505, and define shear lines in the sheath body 505. For example, void 542 defines shear line on one side of the sheath body 505 (not shown), while void 546 defines another shear line 565 on an opposite side of the sheath body 505. In the embodiment shown in FIGS. 5A-5B, the shear lines are approximately sinusoidal due to the position of the peaks and troughs in the S-wires 532, 534 embedded in the sheath body 505 relative to the voids 542, 546. While the shear lines in FIGS. 5A-5B are described as approximately sinusoidal, it will be understood that the shear lines can take on any shape and configuration. As with the sheaths 100, 300 and 400 described in the aforementioned embodiments, the shear lines in FIG. 5B are located within the sheath body 505 and beneath the outer surface of the sheath body 505. When the sheath 500 is subject to a separating force, e.g. when the sheath 500 is pulled apart by a physician, the sheath body 505 is separated into a first portion 550 and a second portion 560. As with the sheaths described in the foregoing, the shear lines define the manner in which the sheath separates when subject to a separating force. Thus shear lines help separate the sheath body 505 into a first portion 550 and a second portion 560 when the sheath 500 is pulled apart.

Figure 6:
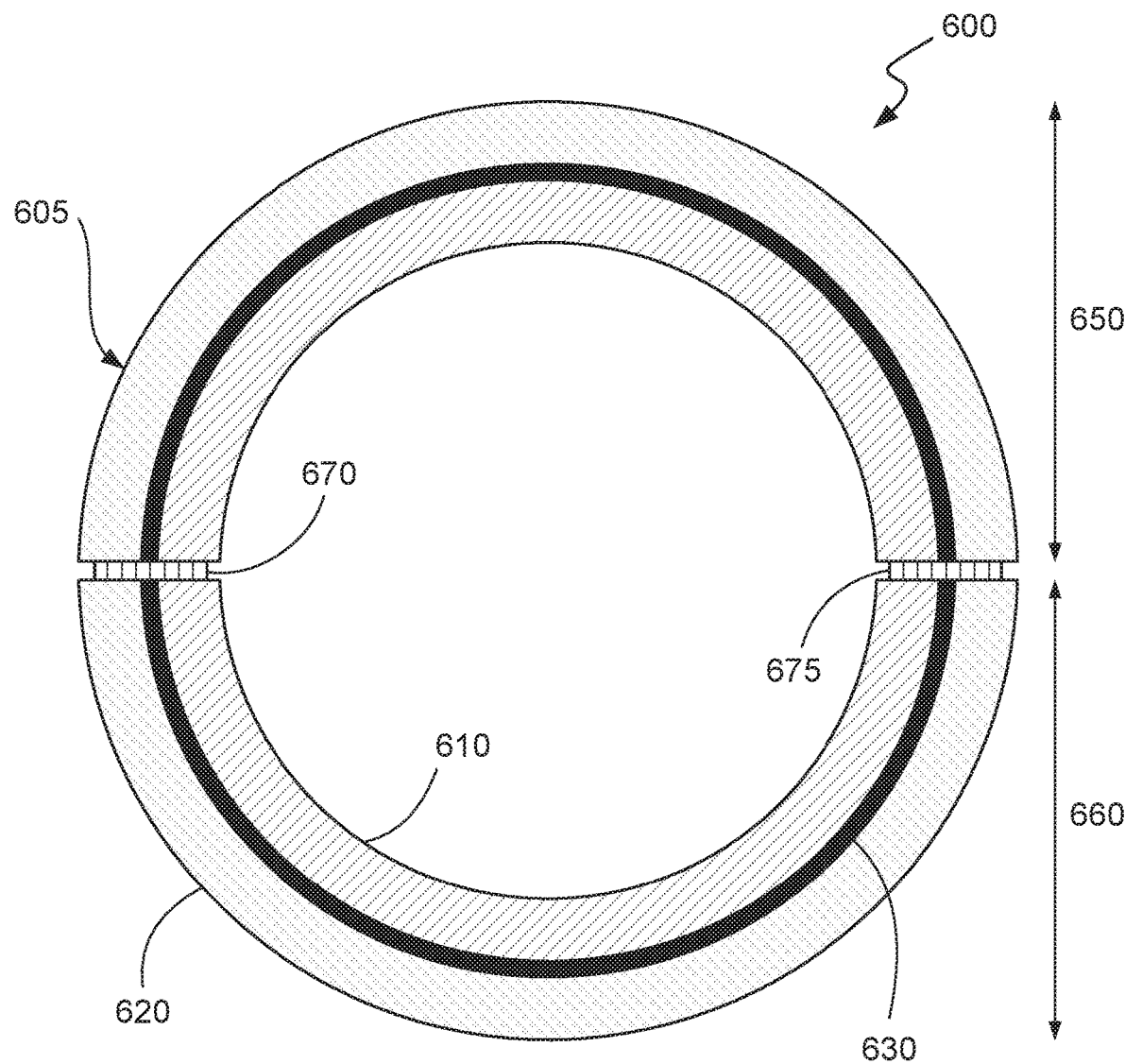
FIG. 6 shows an illustrative cross section of a further embodiment of a kink resistant peel away sheath of the present disclosure involving reflowed separated sheath portions.

FIG. 6 shows a cross section of sheath 600 according to a further embodiment of the present disclosure. Sheath 600 comprises a longitudinal axis that extends into or out of the paper. Unlike the sheaths as described in the foregoing, sheath 600 does not utilize longitudinal voids for the creation of shear lines in the sheath body. Sheath 600 comprises an inner layer 610, an outer layer 620 coaxially arranged about the inner layer 610, and a support layer 630 positioned between the inner layer 610 and the outer layer 630. The support layer 630 may be configured in any manner as described in the foregoing in relation to FIGS. 1-4 and 5A-5B. In the embodiment of FIG. 6, the inner layer 610, outer layer 620 and the support layer 630 are subject to a first reflow treatment that fuses the respective layers together to form sheath body 605.

Sheath body 605 is then split along the longitudinal axis into a first portion 650 and a second portion 660. Sheath body 605 may be split by laser cutting, for example. The first portion 650 and the second portion 660 are then physically reassembled. The physically reassembled sheath body 605 is then subject to a second reflow process. The second reflow process may differ from the first reflow process. For example the temperature profile used may have a lower peak temperature, or the peak temperature used is applied for a smaller time. This second reflow process will cause the first portion 650 and the second portion 660 to fuse together along the edge at which the sheath body 605 was split. This results in the formation of frangible seams 670, 675 along the length of the sheath body 605. The temperature profile of the second reflow process is selected such that when the first portion 650 and the second portion 660 are fused together, the frangible seams 670, 675 are located within sheath body 605 such that the seams 670, 675 do not extend to the outer surface of the sheath body 605, as shown in FIG. 6.

The seams 670, 675 are easily broken upon application of separating forces. Thus the reassembled sheath body 605 is easily separated in the first portion 650 and the second portion 660 when subject to separating forces, e.g. when the sheath 600 is pulled apart by a physician. Seams 670, 675 therefore define shear lines along the sheath body 605 about which the sheath separates. As with the sheaths described in the foregoing, the shear lines define the manner in which the sheath 600 separates when subject to a separating force. The fused inner layer 610, outer layer 620 and support layer 630 of the sheath body 605 improves the flexibility and pushability of the sheath 600 while preventing kinks from forming in the sheath body 605. Additionally the frangible seams 670, 675 enable the sheath body 605 to be easily separated or peeled away. Further, because the frangible seams 670, 675 are located within sheath body 605 such that the seams 670, 675 do not extend to the outer surface of the sheath body 605, the shear lines of sheath 600 are located within the sheath body 605 and beneath the outer surface of the sheath body 605.

Figure 7:
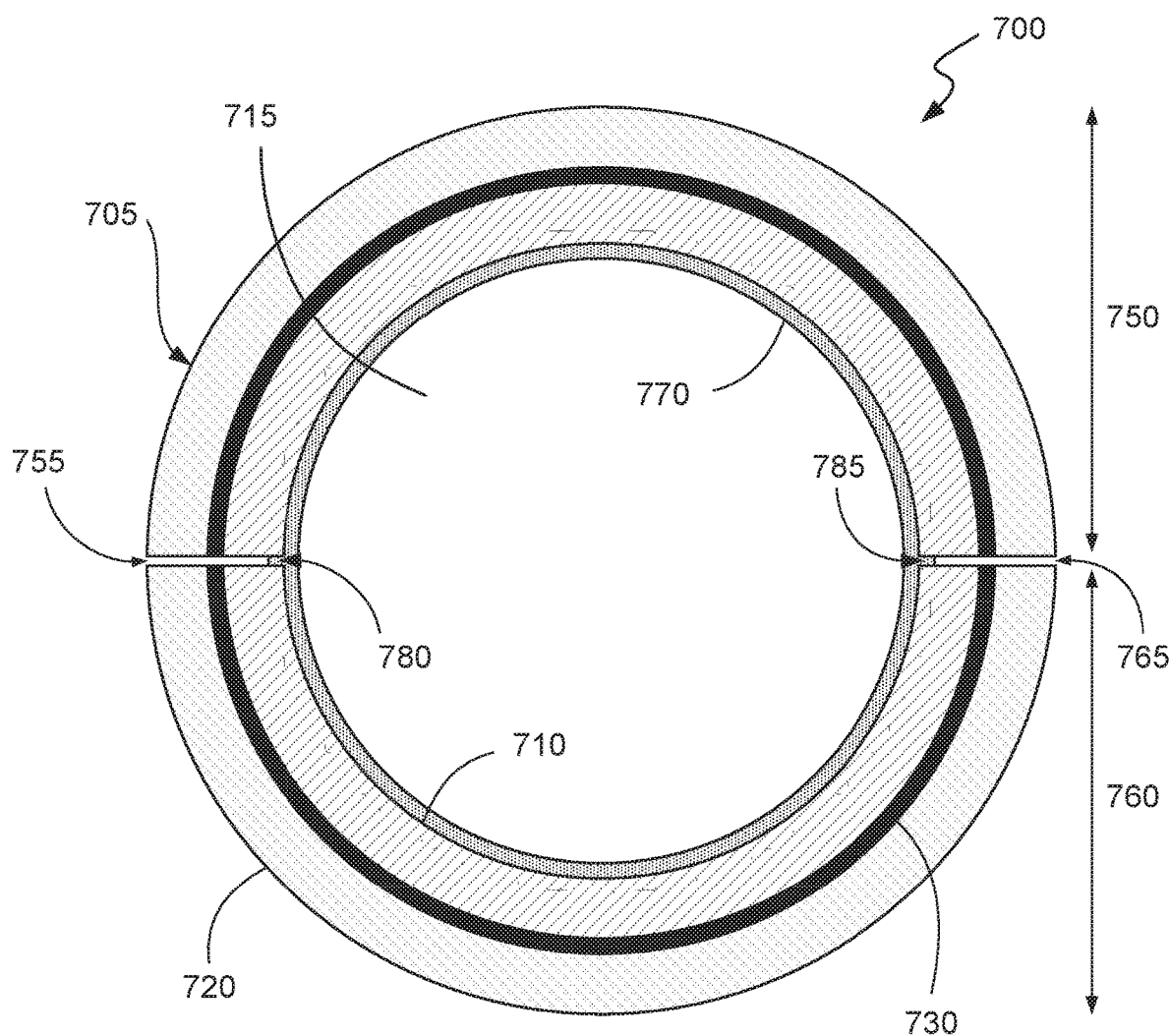
FIG. 7 shows an illustrative cross section of various other embodiments of a kink resistant peel away sheath of the present disclosure involving separated sheath portions that have been reflowed over a thin extruded layer.

FIG. 7 shows a cross section of sheath 700 according to a further embodiment of the present disclosure. Sheath 700 comprises a longitudinal axis that extends into or out of the paper. As with sheath 600 in FIG. 6, sheath 700 does not utilize longitudinal voids for the creation of shear lines in the sheath body. Sheath 700 comprises an inner layer 710 having a lumen 715 running therethrough, an outer layer 720 coaxially arranged about the inner layer 710, and a support layer 730 positioned between the inner layer 710 and the outer layer 730. The support layer 730 may be configured in any manner as described in the foregoing in relation to FIGS. 1-4 and 5A-5B. In the embodiment of FIG. 7, the inner layer 710, outer layer 720 and the support layer 730 are subject to a first reflow treatment that fuses the respective layers together to form sheath body 705.

Sheath body 705 is then split along the longitudinal axis into a first portion 750 and a second portion 760. Sheath body 705 may be split by laser cutting, for example. The first portion 750 and the second portion 760 are then arranged around an extrusion layer 770 comprising a lumen running therethrough. The lumen of the extrusion layer 770 is concentric with lumen 715, the lumen of the extrusion layer having a smaller diameter than lumen 715. The extrusion layer 770 is dimensioned such that when the first portion 750 and the second portion 760 are arranged around the extrusion layer 770, the split edges of the first and second portions do not meet, thereby leaving gaps 755, 765 that extend longitudinally long the sheath body 705. The assembly is then subjected to a second reflow process. The second reflow process may differ from the first reflow process. For example the temperature profile used may have a lower peak temperature, or the peak temperature used is applied for a smaller time. This second reflow process causes the extrusion layer 770 to fuse to the inner surfaces of the first portion 750 and the second portion 760 of the split sheath body 705. This results in the formation of frangible connections 780, 785 in the gaps 755, 765 that extend along the length of the sheath body 705, as shown in FIG. 7. The temperature profile of the second reflow process is selected such that when the first portion 750 and the second portion 760 are fused together, the connections 780, 785 in the gaps 755, 765 are located within sheath body 705 such that the connections 780, 785 do not extend to the outer surface of the sheath body 705, as shown in FIG. 7.

The extrusion layer 770 may have any thickness. Preferably the extrusion layer 770 is thinner than the inner layer 710 and the outer layer 720. In some embodiments the extrusion layer 770 may comprise any one of a polyether block amide (such as PEBAX or PebaSlix®), a polyethylene material, a polytetrafluoroethylene (PTFE) material, a high-density polyethylene (HDPE) material, a medium-density polyethylene (HDPE) material, and a low-density polyethylene (LDPE) material.

The connections 780, 785 are easily broken upon application of separating forces to the first potion 750 and the second portion 760 of the sheath body 705, e.g. when the sheath 700 is pulled apart by a physician. Connections 780, 785 therefore define shear lines along the sheath body 705 about which the sheath 700 separates. In the case of sheath 700, the shear lines coincide with the gaps 755, 765 in the sheath body 705. As with the sheaths described in the foregoing, the shear lines define the manner in which the sheath 700 separates when subject to a separating force. The fused inner layer 710, outer layer 720 and support layer 730 of the sheath body 705 improves the flexibility and pushability of the sheath 700 while preventing kinks from forming in the sheath body 705. The frangible connections 780, 785 enable the sheath body 705 to be easily separated or peeled away. Additionally, because the frangible connections 780, 785 are located within sheath body 705 such that they do not extend to the outer surface of the sheath body 705, the shear lines of sheath 700 are located within the sheath body 705 and beneath the outer surface of the sheath body 705.

Figure 8:
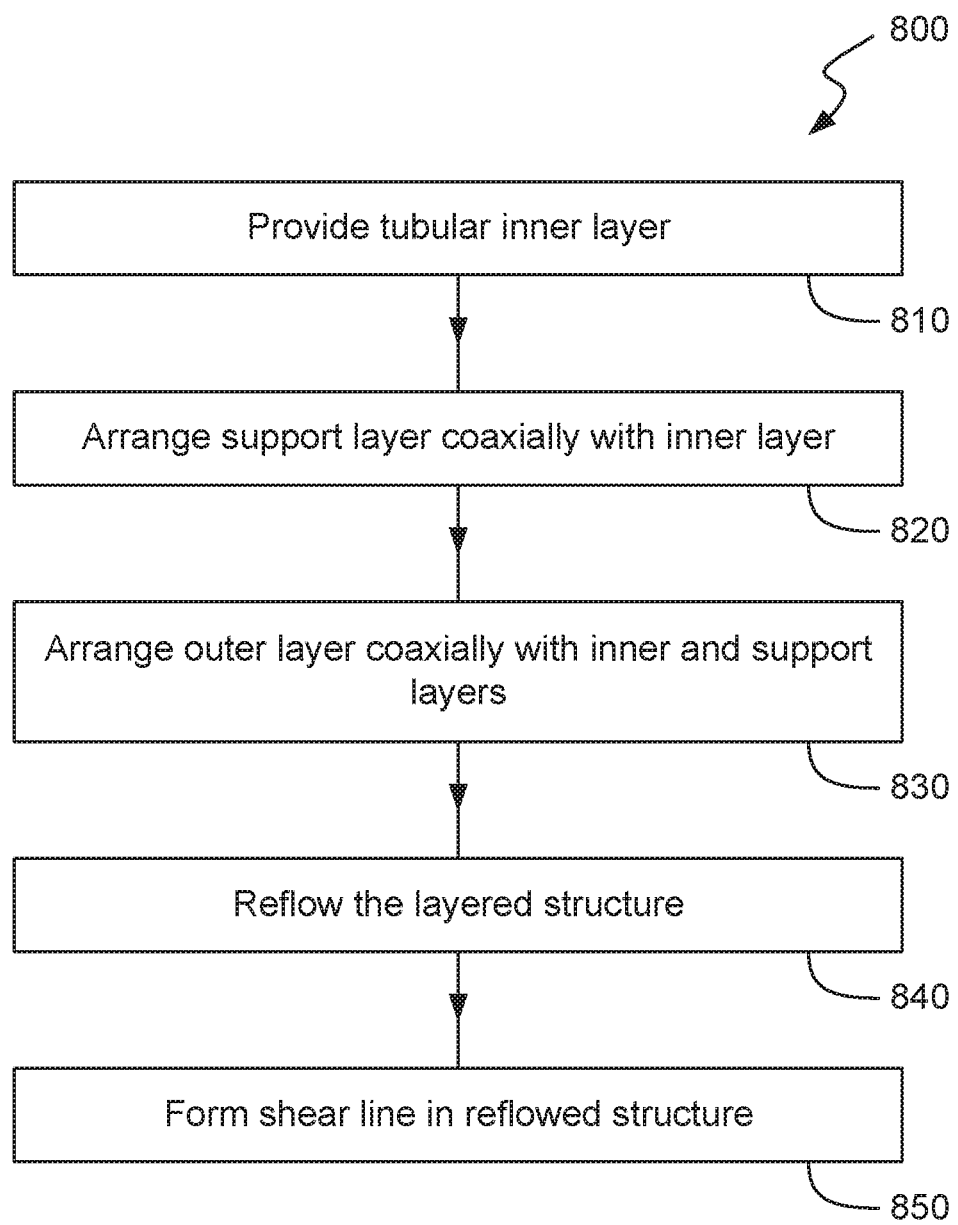
FIG. 8 shows an illustrative flowchart of a method for fabricating a kink resistant peel away sheath according to an embodiment of the present disclosure.

A method of fabricating a kink resistant eel away sheath, such as the sheaths described in the foregoing, will now be described with reference to the method 800 of FIG. 8. The method begins at step 810 in which an inner layer is provided. Here the inner layer comprises an open tubular layer with a lumen running therethrough. The inner layer may comprise a first material. A support layer is then arranged coaxially with the inner layer, per step 820. The support layer may be tubular with a circular cross section. The support layer may comprise a third material. The support layer may comprise a braid structure that reinforces the inner layer, such as support layer 130 as shown in FIG. 1. Alternatively, the support layer may comprise a tubular coil, or at least one S-wire wound around the outer surface of the inner layer that is releasably interlocked with a corresponding number of mandrels, as shown in FIGS. 5A-5B. Further, the support layer may comprise a laser cut extrusion, cut according to any pattern that enhances the pushability of the sheath while keeping it flexible.

In addition to the support layer, monofilaments or rods may optionally be radially positioned on an outer surface of the support layer, such as nylon rods 140, 145, 440, 445 described in relation to FIGS. 1-4. Any number of rods may be used in the layered structure. Preferably, two rods are used, radially separated from each other by 180° about the longitudinal axis of the sheath. The rods may extend linearly along the longitudinal axis of the sheath. In other configurations, the rods may form a helix on the outer surface of the support layer.

In step 830, an outer layer is coaxially arranged over the inner and support layers, to give a layered structure, such as that shown in FIG. 1. If the optional rods are used, the outer layer is arranged so as to contain the inner layer, the support layer and the rods, as shown in FIG. 1. The outer layer may comprise a second material. In some embodiments, the thickness of the inner layer may be equal to the thickness of the outer layer. In other embodiments, the inner layer and the outer layer may be of different thicknesses so as to control the rigidity and flexibility of the sheath. Further, in some embodiments the support layer may be thinner than that of the inner layer and the outer layer. In step 840, the layered structure is subject to a reflow cycle where the layered structure is exposed to heat according to a temperature profile. The heat treatment causes the inner layer, outer layer and support layer to laminate together to form the sheath body as a single fused layer. The lamination of the layers increases the flexibility and pushability of the sheath while preventing kinks from forming in the sheath body. In certain embodiments, the maximum temperature of the reflow cycle is lower that the melting point of nylon. Thus in embodiments where nylon rods are inserted adjacent the outer surface of the support layer (step 820), the rods do not fuse with the remaining layers thereby enabling them to be removed from the sheath body after the reflow process leaving voids in the sheath body in their place, such as voids 142, 146 in FIG. 2. In some embodiments the rods need not be removed from the laminated structure of the sheath body.

In step 850, shear lines are formed in the sheath body. Shear lines comprise lines or voids formed in the sheath body that require minimal force to separate the sheath body. Such shear lines may be formed in regions where the thickness of the sheath body is reduced, such as, for example, by pre-scoring the outer surface of the sheath body with a razor blade. For embodiments that utilize nylon rods during reflow, the sheath body is reduced in thickness in the regions of the nylon rods. Thus when the rods are removed, voids remain in their place in the sheath body. The formation of such voids creates a thinning of the sheath body in the region in close proximity to the voids, thereby forming a shear line. In such embodiments, any separating force applied to the sheath body would naturally cause the sheath body to peel away or tear apart about these thinned regions.

In some embodiments the first material used for the inner layer may comprise any one of a poly ether block amide (such as PEBAX or PebaSlix®), a polyethylene material, a polytetrafluoroethylene (PTFE) material, a high-density polyethylene (HDPE) material, a medium-density polyethylene (MDPE) material, and a low-density polyethylene (LDPE) material. In some embodiments, the second material used for the outer layer may comprise the first material, i.e. the inner layer and the outer layer may be made from the same material. Further, in certain embodiments, the third material used for the support layer may comprise any one of polyether ether ketone (PEEK), a polyether block amide (such as PEBAX or PebaSlix®), a polyethylene material, a polytetrafluoroethylene (PTFE) material, a nylon, a high-density polyethylene (HDPE) material, a medium-density polyethylene (MDPE) material, and a low-density polyethylene (LDPE) material.

Figure 9:
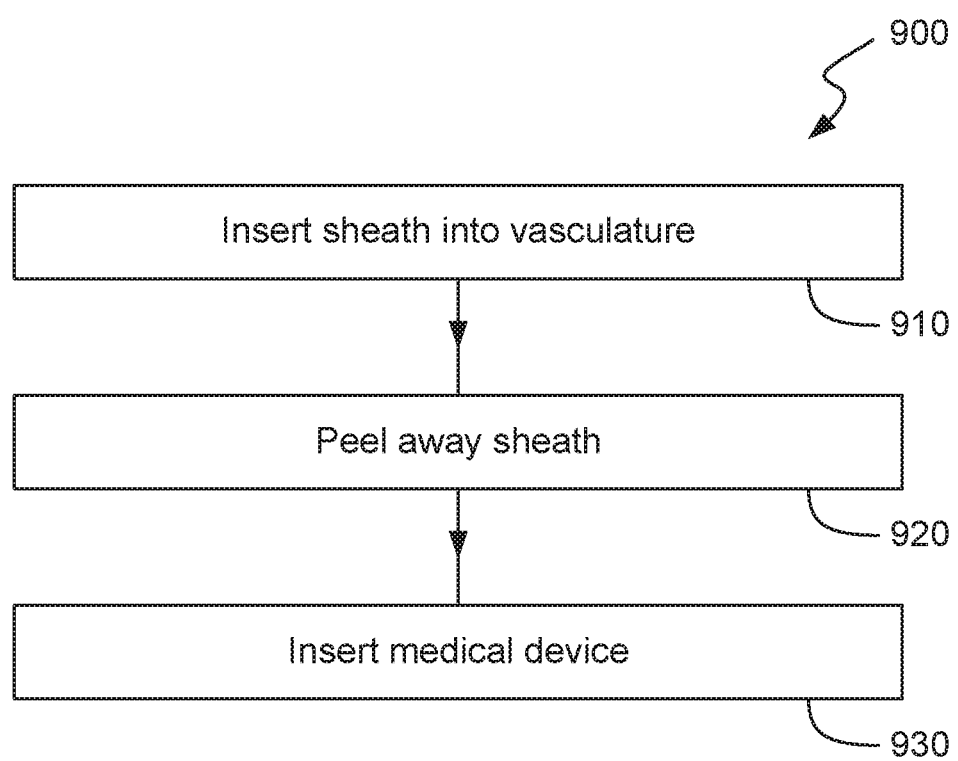
FIG. 9 shows an illustrative flowchart of a method of using a kink resistant peel away sheath according to an embodiment of the present disclosure.

FIG. 9 illustrates an exemplary method 900 of using a kink resistant peel-away sheath, such as any of the sheaths as described in the foregoing, according to an embodiment of the present disclosure. The method 900 begins at step 910 in which the kink resistant peel away sheath is inserted in the arteriotomy of a patient, such as the femoral artery. As previously mentioned, any of the sheaths described in the foregoing may have a tip formed on a patient proximate end of the sheath body. Such a tip may be beveled to aid with insertion into the patient. Due to the laminated structure of the sheath body, the sheath is able to withstand large pushing forces, such as those used to insert the sheath into the patient, without kinking, bending or buckling. In certain embodiments, a dilator may be inserted into the lumen of the sheath before insertion into the patient. The dilator assists with positioning the sheath in regions of the patient's body which are difficult to penetrate with the sheath alone. Once inserted, the dilator is removed from the lumen of the sheath.

At step 920, the inserted sheath is peeled away for the insertion of a medical device into the patient. As mentioned in the foregoing, such a medical device may be a heart pump with a narrow diameter catheter body and a larger diameter pump head. In order to insert the pump head into the arteriotomy of the patient, the sheath needs to be removed or peeled away. In order to peel away the sheath, a separating force is applied on either side of the distal end of the sheath body so as to pull the sheath body apart. Such a separating force may be imparted by a physician. As described in the foregoing, the sheath body contains shear lines located beneath the outer surface of the sheath body, that run along the longitudinal length of the sheath body. Such shear lines are points of weakness in the sheath body structure. Thus when the distal end of the sheath body is subject to a separating force, the sheath body separates or peels away easily. Once the sheath body is peeled away, the larger diameter portion of the medical device, such as the pump head, can be advanced into the arteriotomy of the patient for use, as shown in step 930 of FIG. 9. The use of a peel-away sheath according to the embodiments of the present disclosure allows for the ability of a larger pushing force to be applied to the sheath during positioning without the sheath kinking, bending or buckling, while ensuring that the sheath peels away easily during a medical procedure.

If desired, the different steps discussed herein may be performed in a different order and/or concurrently with each other. Furthermore, if desired, one or more of the above described steps may be optional or may be combined.

The foregoing is merely illustrative of the principles of the disclosure, and the devices and methods can be practiced by other than the described implementations, which are presented for purposes of illustration and not of limitation. It is to be understood that the devices and methods disclosed herein, while shown for use in manufacture of a kink resistant peel-away sheath, may be applied to other systems in which rigid yet flexible open passageways into the vasculature of the patient are required during intravascular procedures.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A sheath for insertion into a vasculature of a patient, the sheath comprising:
a sheath body having an outer surface, a longitudinal axis and a lumen formed therethrough, the sheath body comprising an inner layer arranged about the longitudinal axis, an outer layer coaxially arranged with the inner layer, and a support layer positioned between the inner and outer layers, wherein the inner, outer and support layers are laminated together to form the sheath body; and
at least one shear line formed in the sheath body, the at least one shear line configured to facilitate the longitudinal separation of the sheath body along the at least one shear line,
wherein each of the at least one shear line is defined by a monofilament positioned between the support layer and outer layer, before the inner, outer, and support layers are laminated together such that the at least one shear line, as formed, is positioned beneath the outer surface of the sheath body and within the outer layer.

2. The sheath of claim 1, wherein the inner and outer layers comprise extrusions.

3. The sheath of claim 1, wherein the inner and outer layers are fabricated from at least one of: a polyether block amide, a polyethylene material, a polytetrafluoroethylene (PTFE) material, a high-density polyethylene (HDPE) material, a medium-density polyethylene (MDPE) material, or a low-density polyethylene (LDPE) material.

4. The sheath of claim 1, wherein the at least one shear line is any one of linear or non-linear.

5. The sheath of claim 1, wherein the monofilament is positioned on an outer surface of the support layer and between the support and outer layers.

6. The sheath of claim 5, wherein the monofilament extends longitudinally along the sheath body.

7. The sheath of claim 5, wherein the monofilament helically extends along the longitudinal axis.

8. The sheath of claim 5, wherein the monofilament comprises a rod fabricated from at least one of: polyether ether ketone (PEEK), a polyether block amide, a polyethylene material, a polytetrafluoroethylene (PTFE) material, a nylon, a high-density polyethylene (HDPE) material, a medium-density polyethylene (MDPE) material, a low-density polyethylene (LDPE) material, or stainless steel.

9. The sheath of claim 5, wherein the monofilament is fused with the support layer.

10. The sheath of claim 5, wherein there is a void between the monofilament and the outer layer.

11. The sheath of claim 5, wherein the monofilament is removable from the sheath body.

12. The sheath of claim 1, wherein the at least one shear line comprises a first shear line and a second shear line.

13. The sheath of claim 12, wherein
the first and second shear lines are respectively defined by first and second monofilaments that are each positioned between the support and outer layers, and
the first and second monofilaments are radially separated 180° about the longitudinal axis.

14. The sheath of claim 1, wherein the support layer comprises a braid or a coil.

15. The sheath of claim 1, wherein the support layer comprises a spiral laser cut layer.

16. The sheath of claim 15, wherein the sheath body is pre-scored along the shear line.

17. The sheath of claim 1, wherein the support layer comprises at least one S-shaped wire having turns that are held in an interlocked orientation by a removable mandrel.

18. The sheath of claim 1, wherein the support layer comprises a plurality of S-shaped wires that are held in an interlocked orientation by a corresponding number of removable mandrels.

19. The sheath of claim 1, wherein the at least one shear line extends longitudinally along at least a portion of the length of the sheath body.

20. The sheath of claim 1, wherein the at least one shear line comprises any one of: a void, a frangible seam, or a frangible connection, formed within the sheath body.

21. The sheath of any of claim 1, wherein the support layer is fabricated from at least one of: polyether ether ketone (PEEK), a polyether block amide, a polyethylene material, a polytetrafluoroethylene (PTFE) material, a nylon, a high-density polyethylene (HDPE) material, a medium-density polyethylene (MDPE) material, a low-density polyethylene (LDPE) material, or stainless steel.

22. A method of using the sheath according to claim 1 for treating a patient with a ventricular assist device, the method comprising the steps of:
inserting the sheath into the arteriotomy of the patient at a first position;
inserting the ventricular assist device through the sheath and into the arteriotomy of the patient at the first position; and
separating the sheath by peeling away the sheath body.

* * * * *

UNITED STATES PATENT AND TRADEMARK OFFICE
CERTIFICATE OF CORRECTION

PATENT NO. : 12,083,296 B2
APPLICATION NO. : 16/707923
DATED : September 10, 2024
INVENTOR(S) : Clifford M. Liu It is certified that error appears in the above-identified patent and that said Letters Patent is hereby corrected as shown below:

In the Specification

Column 1, Background, Line 29:
Now reads: "plastic huh"; should read -- plastic hub --

Column 2, Summary, Line 33:
Now reads: "material,"; should read -- material, a --

Column 3, Summary, Line 39:
Now reads: "at leak a"; should read -- at least a --

Column 3, Summary, Line 48:
Now reads: "(HDPE)"; should read -- (MDPE) --

Column 5, Summary, Line 49:
Now reads: "at leak a"; should read -- at least a --

Column 5, Summary, Line 59:
Now reads: "(HDPE)"; should read -- (MDPE) --

Column 6, Brief Description of the Drawings, Line 13:
Now reads: "discloser"; should read -- disclosure --

Column 7, Detailed Description, Line 53:
Now reads: "Massachusetts"; should read -- Massachusetts. --

Column 8, Detailed Description, Line 34:
Now reads: "110"; should read -- 100 --

Signed and Sealed this
Twenty-sixth Day of November, 2024

Katherine Kelly Vidal
*Director of the United States Patent and Trademark Office*

CERTIFICATE OF CORRECTION (continued)
U.S. Pat. No. 12,083,296 B2

Column 8, Detailed Description, Line 57:
Now reads: "material,"; should read -- material, a --

Column 8, Detailed Description, Line 59:
Now reads: "material"; should read -- material, a --

Column 10, Detailed Description, Line 63:
Now reads: "fear"; should read -- tear --

Column 11, Detailed Description, Line 49:
Now reads: "When"; should read -- when --

Column 11, Detailed Description, Line 58:
Now reads: "it s understood"; should read -- it is understood --

Column 11, Detailed Description, Line 64:
Now reads: "shear body"; should read -- sheath body --

Column 14, Detailed Description, Line 3:
Now reads: "630."; should read -- 620. --

Column 14, Detailed Description, Line 58:
Now reads: "730."; should read -- 720. --

Column 15, Detailed Description, Line 33:
Now reads: "(HDPE)"; should read -- (MDPE) --

Column 15, Detailed Description, Line 36:
Now reads: "first potion"; should read -- first portion --

Column 15, Detailed Description, Line 56:
Now reads: "eel away"; should read -- peel away --

Column 16, Detailed Description, Line 62:
Now reads: "poly ether"; should read -- polyether --